(12) United States Patent
Krapohl et al.

(10) Patent No.: US 9,033,973 B2
(45) Date of Patent: May 19, 2015

(54) SYSTEM AND METHOD FOR DC TISSUE IMPEDANCE SENSING

(75) Inventors: James E. Krapohl, Broomfield, CO (US); Robert B. Smith, Loveland, CO (US); Mark A. Johnston, Boulder, CO (US)

(73) Assignee: Covidien LP, Mansfield, MA (US)

( * ) Notice: Subject to any disclaimer, the term of this patent is extended or adjusted under 35 U.S.C. 154(b) by 883 days.

(21) Appl. No.: 13/221,424

(22) Filed: Aug. 30, 2011

(65) Prior Publication Data

US 2013/0053840 A1 Feb. 28, 2013

(51) Int. Cl.
*A61B 18/12* (2006.01)
*A61B 18/18* (2006.01)
(Continued)

(52) U.S. Cl.
CPC ............. *A61B 18/18* (2013.01); *A61B 18/1206* (2013.01); *A61B 18/1402* (2013.01); *A61B 18/1445* (2013.01); *A61B 2018/00642* (2013.01); *A61B 2018/00702* (2013.01); *A61B 2018/00708* (2013.01); *A61B 2018/00827* (2013.01); *A61B 2018/00875* (2013.01); *A61B 2018/00892* (2013.01); *A61B 2018/00898* (2013.01)

(58) Field of Classification Search
CPC .......... A61B 18/1206; A61B 18/1402; A61B 18/1445; A61B 2018/00642; A61B 2018/00702; A61B 2018/00827; A61B 2018/00892
USPC .............................................. 606/27, 34, 41
See application file for complete search history.

(56) References Cited

U.S. PATENT DOCUMENTS

| 4,569,345 | A |   | 2/1986  | Manes                    |
|-----------|---|---|---------|--------------------------|
| 4,727,874 | A | * | 3/1988  | Bowers et al. ... 606/38 |
| 4,878,493 | A | * | 11/1989 | Pasternak et al. ... 607/99 |

(Continued)

FOREIGN PATENT DOCUMENTS

| DE | 179607  | 3/1905 |
|----|---------|--------|
| DE | 1099658 | 2/1961 |

(Continued)

OTHER PUBLICATIONS

U.S. Appl. No. 10/406,690, filed Apr. 3, 2003, Robert J. Behnke, II.

(Continued)

*Primary Examiner* — Michael Peffley
*Assistant Examiner* — Daniel Fowler

(57) ABSTRACT

A system and method for transmitting electrosurgical energy from a generator to an electrosurgical instrument are provided. The electrosurgical system includes a generator adapted to generate electrosurgical energy for treating tissue. The generator includes one or more active output terminals which supply energy to the tissue. The active output terminals are operatively connected to one or more active leads. The generator also includes one or more return output terminals which returns energy from the tissue. The return output terminals are operatively connected to at least one return lead. The system also includes an electrosurgical instrument operatively connected to the one or more active leads and one or more return electrodes operatively connected to one or more return leads. The system further includes an electrosurgical cable including one or more active leads and one or more return leads. The one or more active leads and one or more return leads are wound in a double helix fashion such that the electrical field along the cable is mitigated along the length thereof.

12 Claims, 5 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 5,334,193 A | 8/1994 | Nardella | |
| 5,422,567 A | 6/1995 | Matsunaga | |
| 5,484,400 A * | 1/1996 | Edwards et al. | 604/22 |
| 5,540,681 A * | 7/1996 | Strul et al. | 606/34 |
| 5,558,671 A | 9/1996 | Yates | |
| 5,707,369 A | 1/1998 | Vaitekunas et al. | |
| 5,720,744 A | 2/1998 | Eggleston et al. | |
| 5,772,659 A | 6/1998 | Becker et al. | |
| 5,792,138 A | 8/1998 | Shipp | |
| 5,810,804 A | 9/1998 | Gough et al. | |
| 6,059,780 A | 5/2000 | Gough et al. | |
| 6,142,992 A | 11/2000 | Cheng et al. | |
| 6,193,713 B1 * | 2/2001 | Geistert et al. | 606/34 |
| 6,203,541 B1 | 3/2001 | Keppel | |
| 6,238,387 B1 * | 5/2001 | Miller, III | 606/34 |
| 6,251,106 B1 | 6/2001 | Becker et al. | |
| 6,258,085 B1 | 7/2001 | Eggleston | |
| 6,293,941 B1 | 9/2001 | Strul et al. | |
| 6,370,408 B1 | 4/2002 | Merchant et al. | |
| 6,402,742 B1 | 6/2002 | Blewett et al. | |
| 6,458,121 B1 | 10/2002 | Rosenstock et al. | |
| 6,544,260 B1 | 4/2003 | Markel et al. | |
| 6,565,559 B2 | 5/2003 | Eggleston | |
| 6,706,038 B2 * | 3/2004 | Francischelli et al. | 606/34 |
| 6,784,405 B2 | 8/2004 | Flugstad et al. | |
| 6,875,210 B2 | 4/2005 | Refior et al. | |
| 6,936,047 B2 | 8/2005 | Nasab et al. | |
| 6,948,503 B2 | 9/2005 | Refior et al. | |
| 6,953,461 B2 | 10/2005 | McClurken et al. | |
| 7,041,096 B2 | 5/2006 | Malis et al. | |
| 7,060,063 B2 | 6/2006 | Marion et al. | |
| 7,101,373 B2 * | 9/2006 | Dycus et al. | 606/51 |
| 7,146,210 B2 | 12/2006 | Palti | |
| 7,169,144 B2 | 1/2007 | Hoey et al. | |
| 7,247,155 B2 | 7/2007 | Hoey et al. | |
| 7,250,048 B2 | 7/2007 | Francischelli et al. | |
| 7,367,972 B2 | 5/2008 | Francischelli et al. | |
| D574,323 S | 8/2008 | Waaler | |
| 7,422,582 B2 | 9/2008 | Malackowski et al. | |
| 7,927,328 B2 | 4/2011 | Orszulak et al. | |
| 7,956,620 B2 | 6/2011 | Gilbert | |
| 7,976,544 B2 | 7/2011 | McClurken et al. | |
| 8,034,049 B2 | 10/2011 | Odom et al. | |
| 8,045,943 B2 | 10/2011 | Kaczman et al. | |
| 2003/0181898 A1 * | 9/2003 | Bowers | 606/34 |
| 2007/0129716 A1 | 6/2007 | Daw et al. | |
| 2007/0173803 A1 | 7/2007 | Wham et al. | |
| 2007/0173806 A1 | 7/2007 | Orszulak et al. | |
| 2007/0173813 A1 | 7/2007 | Odom | |
| 2008/0039831 A1 | 2/2008 | Odom et al. | |
| 2008/0082096 A1 | 4/2008 | Shores et al. | |
| 2008/0082100 A1 | 4/2008 | Orton et al. | |
| 2008/0281311 A1 | 11/2008 | Dunning et al. | |
| 2009/0234350 A1 | 9/2009 | Behnke et al. | |
| 2009/0292283 A1 | 11/2009 | Odom | |
| 2009/0306648 A1 | 12/2009 | Podhajsky et al. | |
| 2010/0016857 A1 | 1/2010 | McKenna et al. | |
| 2010/0042093 A9 | 2/2010 | Wham et al. | |
| 2010/0079215 A1 | 4/2010 | Brannan et al. | |
| 2010/0082022 A1 | 4/2010 | Haley et al. | |
| 2010/0082023 A1 | 4/2010 | Brannan et al. | |
| 2010/0082024 A1 | 4/2010 | Brannan et al. | |
| 2010/0082025 A1 | 4/2010 | Brannan et al. | |
| 2010/0082083 A1 | 4/2010 | Brannan et al. | |
| 2010/0082084 A1 | 4/2010 | Brannan et al. | |
| 2010/0094271 A1 | 4/2010 | Ward et al. | |
| 2010/0179534 A1 | 7/2010 | Podhajsky et al. | |
| 2010/0179535 A1 | 7/2010 | Podhajsky et al. | |
| 2010/0179538 A1 | 7/2010 | Podhajsky | |
| 2011/0037484 A1 | 2/2011 | Gilbert | |
| 2011/0071516 A1 | 3/2011 | Gregg | |
| 2011/0071521 A1 | 3/2011 | Gilbert | |
| 2011/0077631 A1 | 3/2011 | Keller | |
| 2011/0144635 A1 | 6/2011 | Harper et al. | |
| 2011/0178516 A1 | 7/2011 | Orszulak et al. | |
| 2011/0204903 A1 | 8/2011 | Gilbert | |
| 2013/0035679 A1 | 2/2013 | Orszulak | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1151725 | 11/2001 |
| EP | 1366724 | 1/2006 |
| EP | 880220 | 6/2006 |
| EP | 1681026 A2 | 7/2006 |
| EP | 1776929 | 4/2007 |
| EP | 1810630 | 7/2007 |
| EP | 2042116 A1 | 4/2009 |
| EP | 1810632 | 6/2009 |
| EP | 1810628 | 7/2009 |
| EP | 2393208 A2 | 12/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 2000271145 A | 10/2000 |
| JP | 2006506172 A | 2/2006 |
| SU | 166452 | 1/1965 |
| SU | 727201 | 4/1980 |
| WO | WO95/09577 | 4/1995 |
| WO | WO96/39085 | 12/1996 |
| WO | WO97/06739 | 2/1997 |
| WO | WO97/06740 | 2/1997 |
| WO | WO97/06855 | 2/1997 |
| WO | WO97/11648 | 4/1997 |
| WO | 9847436 A1 | 10/1998 |
| WO | WO00/48672 | 8/2000 |
| WO | WO02/11634 | 2/2002 |
| WO | WO02/45589 | 6/2002 |

(56) References Cited

FOREIGN PATENT DOCUMENTS

| WO | WO03/090635 | 11/2003 |
|---|---|---|
| WO | WO2004/004340 | 1/2004 |
| WO | WO2006/050888 | 5/2006 |
| WO | WO2006/105121 | 10/2006 |
| WO | WO2007/067522 | 6/2007 |
| WO | 2008/043999 A2 | 4/2008 |
| WO | WO2008/043999 | 4/2008 |
| WO | WO2008/044013 | 4/2008 |
| WO | WO2008/053532 | 5/2008 |
| WO | WO2008/071914 | 6/2008 |
| WO | WO2008/110756 | 9/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 21, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Wald et al., "Accidental Burns", JAMA, Aug. 16, 1971, vol. 217, No. 7, pp. 916-921.
Vallfors et al, "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.

Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.

(56) References Cited

OTHER PUBLICATIONS

International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
International Search Report and Written Opinion from PCT Appl. No. PCT/US2012/051796 mailed Jan. 24, 2013.
European Search Report No. 14166165.2 dated Jul. 8, 2014.
European Search Report Application No. EP 12 82 7271, dated Mar. 4, 2015.

\* cited by examiner

SYSTEM AND METHOD FOR DC TISSUE IMPEDANCE SENSING

BACKGROUND

1. Technical Field

The present disclosure relates to an electrosurgical system and method for performing electrosurgical procedures. More particularly, the present disclosure relates to a system and method for detecting direct current (DC) properties (e.g., voltage and current) within an electrosurgical generator and controlling output of radio frequency treatment energy based on the measured DC properties.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes prevents current flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive surfaces which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

Electrosurgical procedures outlined above may utilize various tissue and energy parameters in a feedback-based control system. There is continual need to improve sensors as well as systems and method for processing the sense signals.

SUMMARY

In one embodiment, the present disclosure provides for an electrosurgical system. The system includes a direct current power supply configured to supply direct current; a radio frequency output stage electrically coupled to the direct current power supply, the radio frequency output stage configured to transform direct current into a radio frequency waveform; a direct current voltage sensor coupled to the direct current power supply and configured to measure direct current voltage; a direct current current sensor coupled to the direct current power supply and configured to measure direct current; and a controller coupled to the direct current voltage and current sensors, the controller configured to determine at least one of voltage and current of the radio frequency waveform based on the measured voltage and current of the direct current.

In another embodiment, the present disclosure provides for a method for delivering radio frequency energy to tissue. The method includes generating direct current at a direct current power supply; transforming direct current into a radio frequency waveform at a radio frequency output stage electrically coupled to the direct current power supply; measuring voltage and current of the direct current supplied to the radio frequency output stage; and determining at least one of voltage and current of the radio frequency waveform based on the measured voltage and current of the direct current.

In further embodiments, an electrosurgical system is disclosed. The system includes an electrosurgical generator having a direct current power supply configured to supply direct current; a direct current voltage sensor coupled to the direct current power supply and configured to measure direct current voltage; a direct current current sensor coupled to the direct current power supply and configured to measure direct current; and a controller coupled to the direct current voltage and current sensors. The system also includes an electrosurgical instrument coupled to the electrosurgical generator, the electrosurgical instrument including a radio frequency output stage electrically coupled to the direct current power supply, the radio frequency output stage configured to transform direct current into a radio frequency waveform, wherein the controller is configured to determine at least one of voltage and current of the radio frequency waveform based on the measured voltage and current of the direct current.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A generator according to the present disclosure can perform monopolar and/or bipolar electrosurgical procedures, including vessel sealing procedures. The generator may include a plurality of outputs for interfacing with various electrosurgical instruments (e.g., a monopolar instrument, return electrode, bipolar electrosurgical forceps, footswitch, etc.). Further, the generator includes electronic circuitry configured to generate radio frequency energy specifically suited for various electrosurgical modes (e.g., cutting, blending, division, etc.) and procedures (e.g., monopolar, bipolar, vessel sealing). In embodiments, the generator may be embedded, integrated or otherwise coupled to the electrosurgical instruments providing for an all-in-one electro surgical apparatus.

Figure 1:
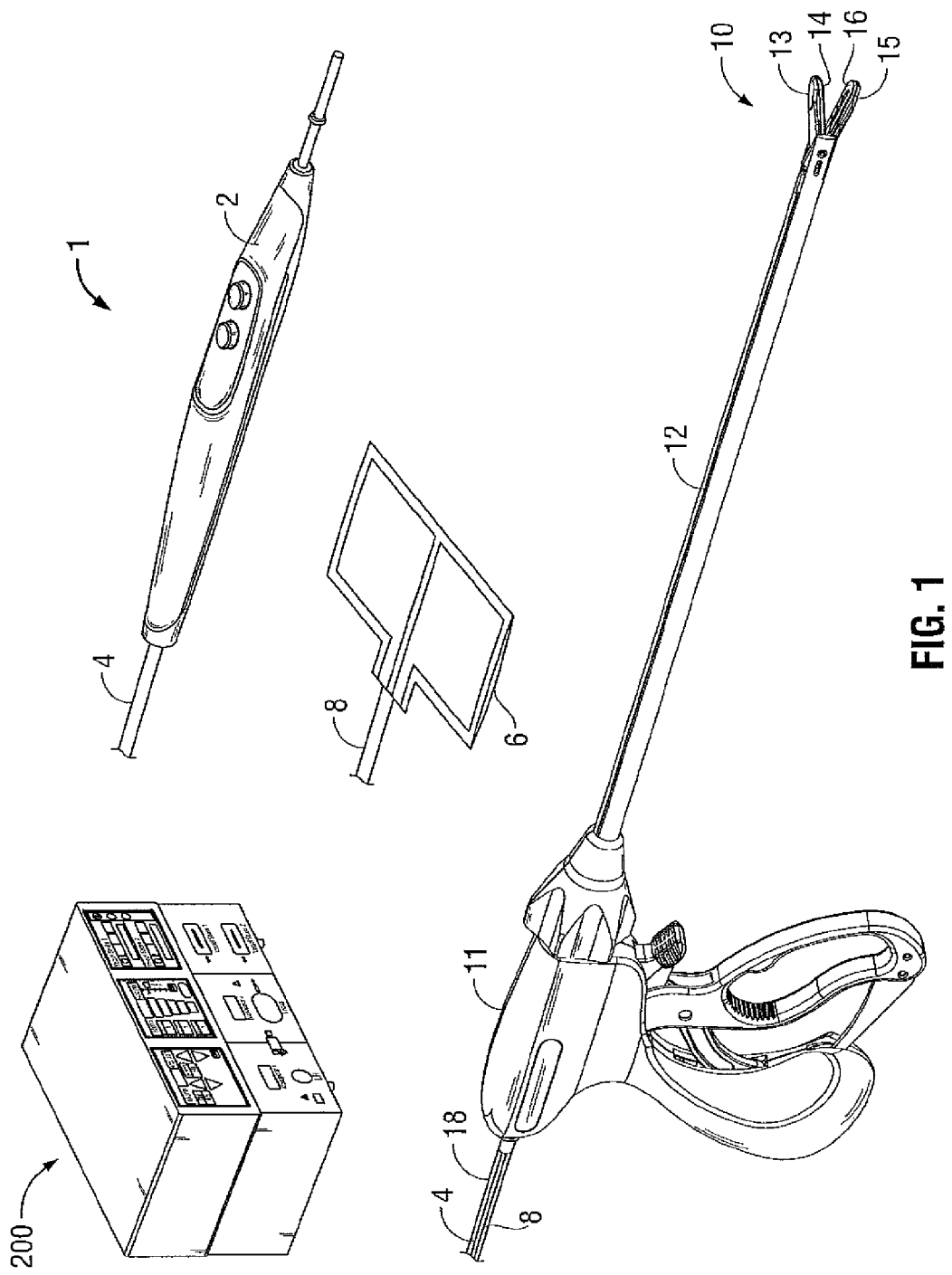
FIG. 1 is a schematic block diagram of an embodiment of an electrosurgical system according to the present disclosure.

FIG. 1 is a schematic illustration of a bipolar and monopolar electrosurgical system 1 according to the present disclosure. The system 1 may include one or more monopolar electrosurgical instruments 2 having one or more electrodes (e.g., electrosurgical cutting probe, ablation electrode(s), etc.) for treating tissue of a patient. Electrosurgical energy is supplied to the instrument 2 by a generator 200 via a supply line 4 that is connected to an active terminal 230 (FIG. 3) of the generator 200, allowing the instrument 2 to coagulate, ablate and/or otherwise treat tissue. The energy is returned to the generator 200 through a return electrode 6 via a return line 8 at a return terminal 32 (FIG. 3) of the generator 200. The system 1 may include a plurality of return electrodes 6 that are disposed on a patient to minimize the chances of tissue damage by maximizing the overall contact area with the patient. In addition, the generator 200 and the return electrode 6 may be configured for monitoring so-called "tissue-to-patient" contact to insure that sufficient contact exists therebetween to further minimize chances of tissue damage.

Figure 3:
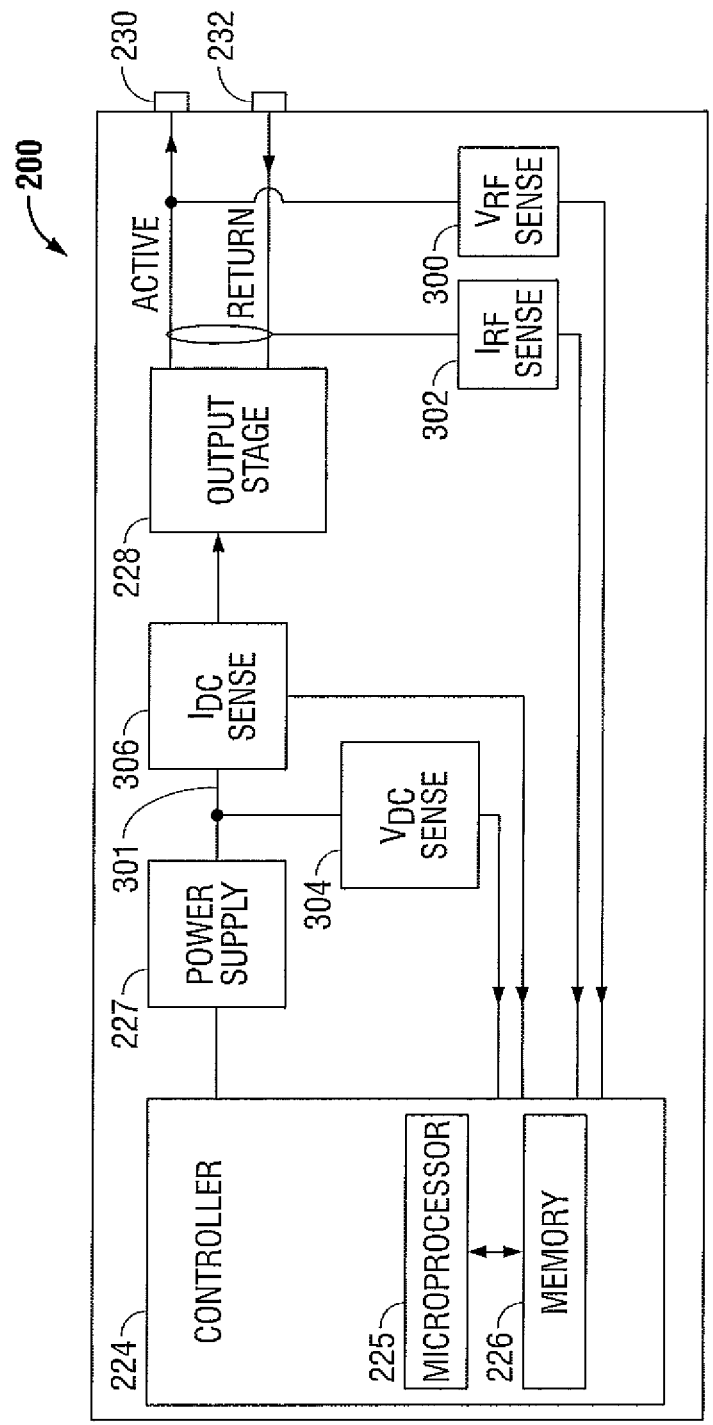
FIG. 3 is a schematic block diagram of the electrosurgical generator of FIG. 2 according to the present disclosure.

The system 1 may also include a bipolar electrosurgical forceps 10 having one or more electrodes for treating tissue of a patient. The electrosurgical forceps 10 includes a housing 11 and opposing jaw members 13 and 15 disposed at a distal end of a shaft 12. The jaw members 13 and 15 have one or more active electrodes 14 and a return electrode 16 disposed therein, respectively. The active electrode 14 and the return electrode 16 are connected to the generator 200 through cable 18 that includes the supply and return lines 4, 8 coupled to the active and return terminals 230, 232, respectively (FIG. 3). The electrosurgical forceps 10 is coupled to the generator 200 at a connector having connections to the active and return terminals 230 and 232 (e.g., pins) via a plug disposed at the end of the cable 18, wherein the plug includes contacts from the supply and return lines 4, 8 as discussed in more detail below.

Figure 2:
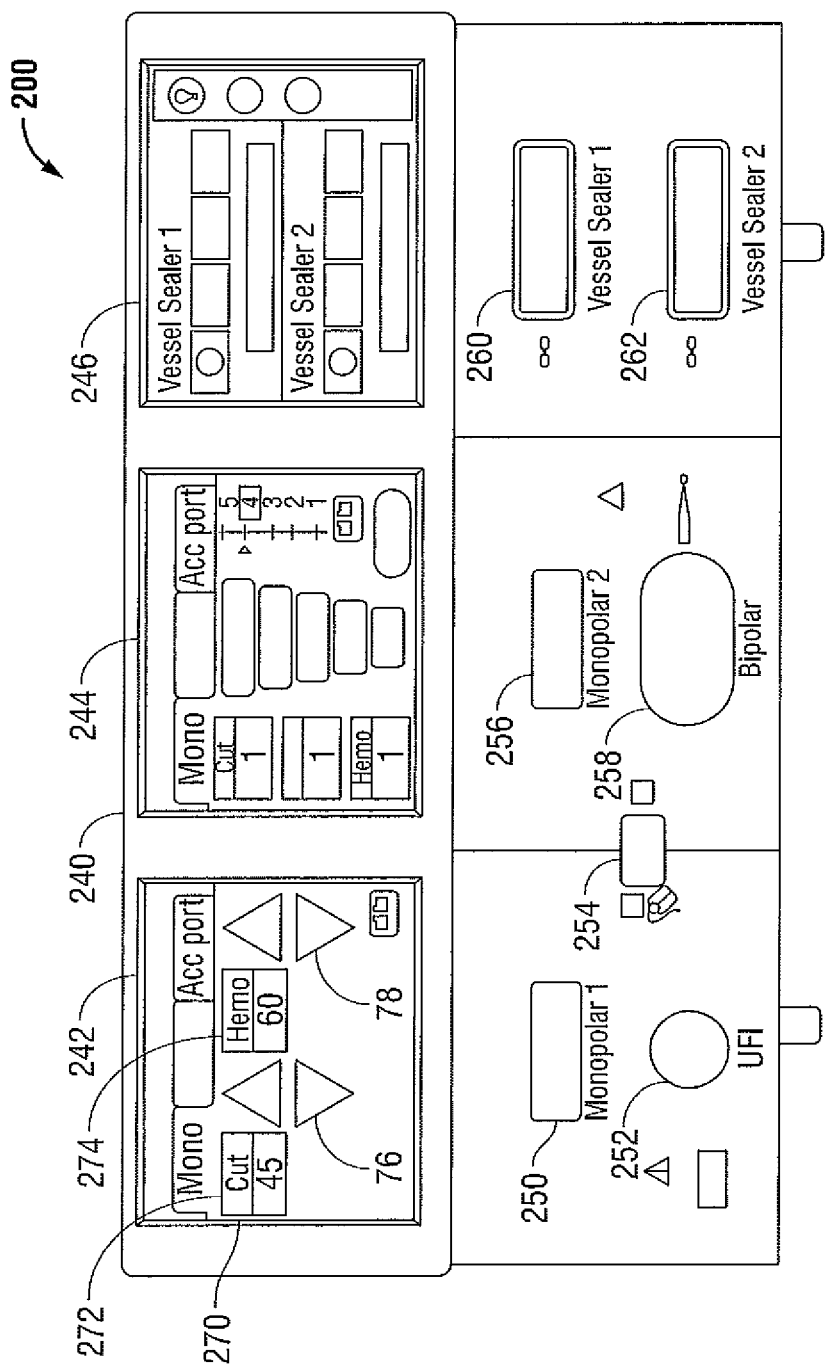
FIG. 2 is a front view of an electrosurgical generator according to the present disclosure.

With reference to FIG. 2, a front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read (e.g., scan, decode, etc.) identifying information encoded or otherwise recorded on or within the plugs or cables of the instruments. The connectors 250-262 are configured to decode the information encoded on the plugs corresponding to the operating parameters of particular instruments allowing the generator 200 to preset energy delivery settings based on the connected instrument. In embodiments, data may be encoded in bar codes, electrical components (e.g., resistors, capacitors, etc.), RFID chips, magnets, non-transitory storage (e.g., non-volatile memory, EEPROM, etc.), which may then be coupled to or integrated into the plug. Corresponding detection devices may include, but are not limited to, bar code readers, electrical sensors, RFID readers, Hall Effect sensors, memory readers, etc. and any other suitable decoders configured to decode data.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then makes inputs by simply touching corresponding menu options.

Screen 242 controls monopolar output and the devices connected to the connectors 250 and 252. Connector 250 is configured to couple to monopolar electrosurgical instrument (e.g., electrosurgical pencil) and connector 252 is configured to couple to a foot switch (not shown). The foot switch provides for additional inputs (e.g., replicating inputs of the generator 200). Screen 244 controls monopolar and bipolar output and the devices connected to the connectors 256 and 258. Connector 256 is configured to couple to other monopolar instruments. Connector 258 is configured to couple to a bipolar instrument (not shown).

Screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with an output curve of the generator 200. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. The generator 200 includes a controller 224, a power supply 227, and an output stage 228. The power supply 227 may be a direct current high voltage power supply and is connected to an AC source (e.g., line voltage) and provides high voltage DC power to an output stage 228, which then converts high voltage DC power into treatment energy (e.g., ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may include transitory type memory (e.g., RAM) and/or non-transitory type memory (e.g., flash media, disk media, etc.). The microprocessor 225 includes an output port that is operably connected to the power supply 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations discussed herein.

A closed loop control scheme is a feedback control loop, in which a plurality of sensors measure a variety of tissue and energy properties (e.g., tissue impedance, tissue temperature, output power, current and/or voltage, etc.), and provide feedback to the controller 224. The controller 224 then signals the power supply 227 and/or output stage 228, which then adjusts the DC and/or power supply, respectively. The controller 224 also receives input signals from the input controls of the generator 200, the instrument 2 and/or forceps 10. The controller 224 utilizes the input signals to adjust power outputted by the generator 200 and/or performs other control functions thereon.

The generator 200 according to the present disclosure includes an RF voltage sensor 300 and an RF current sensor 302. The RF voltage sensor 300 is coupled to the active and return terminals 230 and 232 provides measurements of the RF voltage supplied by the output stage 228. The RF current sensor 302 is coupled to the active terminal 230 and provides measurements of the RF current supplied by the output stage 228. The RF voltage and current sensors 230 and 232 may be any suitable RF voltage/current sensor including, but not limited to, sense transformers, sense resistors, sense capacitors, and combinations thereof. The RF voltage and current sensors 300 and 302 provide the sensed RF voltage and current signals, respectively, to the controller 224, which then may adjust output of the power supply 227 and/or the output stage 228 in response to the sensed RF voltage and current signals.

The generator 200 according to the present disclosure also includes a DC voltage sensor 304 and a DC current sensor 306. For simplicity, the power supply 227 is shown schematically being coupled to the output stage 228 via a connection 301. Those skilled in the art will appreciate that the power supply 227 is connected with its positive and negative terminals (not shown) to the output stage 228. The DC voltage and current sensors 304 and 306 are coupled to the connection 301 and provide measurements of the DC voltage and current supplied to the output stage 228 by the power supply 227. The DC voltage and current sensors 304 and 306 may be any suitable DC voltage/current sensor including, but not limited to, Hall Effect sensors, sense resistors, and combinations thereof. The DC voltage and current sensors 304 and 306 provide the sensed DC voltage and current signals, respectively, to the controller 224, which then may adjust output of the power supply 227 and/or the output stage 228 in response to the sensed DC voltage and current signals.

The output stage 228 may be embodied as any suitable RF inverter power supply topology including, but not limited to, half bridge, full bridge, push pull, and combinations thereof. In embodiments, the output of the output stage 228 may be any amplitude-modulated RF waveform generated by varying DC voltage of the power supply 227. The generator 200 adjusts the RF output of the output stage 228 based on the sensed signals as measured by either the DC voltage and current sensors 304 and 306 and/or the RF voltage and current sensors 300 and 302.

The controller 224 includes a transfer function that correlates the sensed DC voltage and current signals to the sensed RF voltage and current signals. In particular, the operating parameters of the output stage 228 may be expressed as a transfer function, which may be used to calculate output RF voltage and current based on the sensed DC voltage and current signals. The transfer function may be used to compensate for the loss and/or distortion introduced between the output stage 228 and the load. These non-ideal behaviors can be impacted by many different factors including input voltage, input current, output voltage, output current and load impedance. One way to characterize these behaviors may include analysis of the generator 200 at different open loop operating points while monitoring the input and/or output characteristics, namely, DC voltage and current and RF output voltage and current. This data may then be used to generate a polynomial curve fit and/or piecewise linear curve. The curves are then transposed to a transfer function that describes the relationship between the DC voltage and current and the output RF voltage and current thus providing the transfer function. The process to obtain the transfer function may be performed during initial setup of the generator 200 on a unit-by-unit basis or for any specific lot and then preprogrammed and stored in memory 226.

Thus, the controller 224 determines the output RF voltage and current based on the sensed DC voltage and current signals. The calculated output RF voltage and current may then be compared with actual sensed RF voltage and current as a redundant measurement (e.g., to verify functionality of the sensors 300, 302, 304, and 306).

Figure 4:
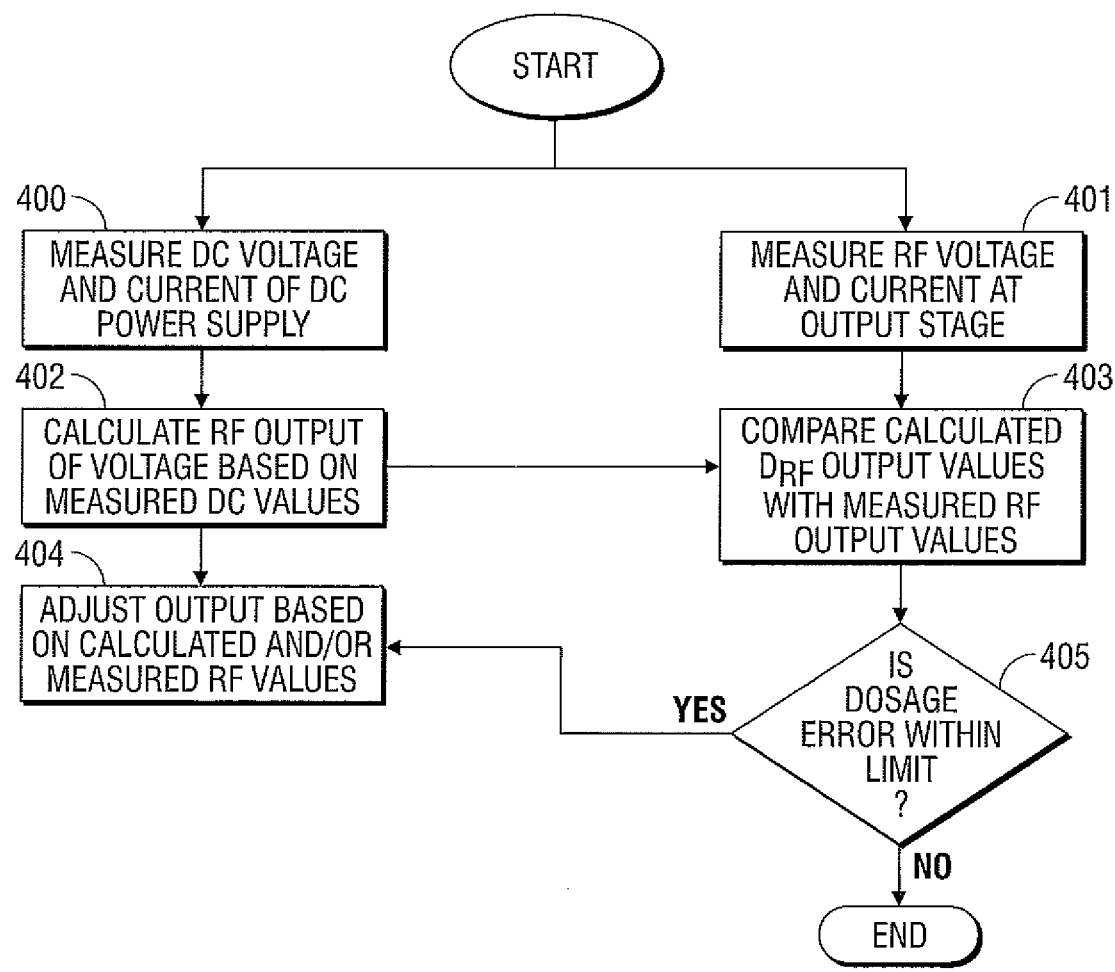
FIG. 4 is a flow chart of a method according to the present disclosure.

FIG. 4 illustrates a method in accordance with the present disclosure. In step 400, DC voltage and current outputted by the power supply 227 are measured by the DC voltage and current sensors 304 and 306, respectively. The measured sensor signals are transmitted to the controller 224. In step 402, the controller 224 calculates the output RF voltage and current based on the sensed DC voltage and current values. In particular, the controller 224 (e.g., the microprocessor 225) utilizes a transfer function that correlates the sensed output DC values with output RF values.

In step 401, RF voltage and current outputted by the output stage 228 are measured by the RF voltage and current sensors 300 and 302, respectively. The measured sensor signals are transmitted to the controller 224. In step 403, the controller 224 compares measured RF output values with the calculated the RF voltage and current based on the sensed DC voltage and current values. The difference between calculated RF values and measured RF values may be used to determine functionality of the generator 200, such that if the difference between the measured and calculated RF values varies by a predetermined amount an error is issued resulting in stoppage and/or adjustment of the power output. The difference between calculated and measured RF values which triggers an error condition may be from about 10% and above, in embodiments, from about 20% and above.

In step 405, the controller 224 may utilize the comparison to determine dosage error in delivery of output power. The term "dosage error" as used herein denotes a difference between preset output power (e.g., user or generator selected) and delivered output power. The difference may be due to a variety of factors (e.g., malfunctioning power generating components, sensors, etc.). The dosage error, e.g., difference between preset power and calculated RF values based on measured DC values and/or actual measured RF values may be from about 10% and above, in embodiments, from about 20% and above. The dosage error calculation determines the functionality (or malfunction) of the sensors 300, 302, 304, and 306. Thus, if the dosage error is outside a desired limit, in step 405, the controller 224 may issue an alarm and/or terminate the output of the generator 200.

In step 404, the controller 224 signals the power supply 227 and/or the output stage 228 to adjust its output in response to an algorithm or other instructions for controlling the output of the generator 200 including differences calculated in steps 403 and 405.

Figure 5:
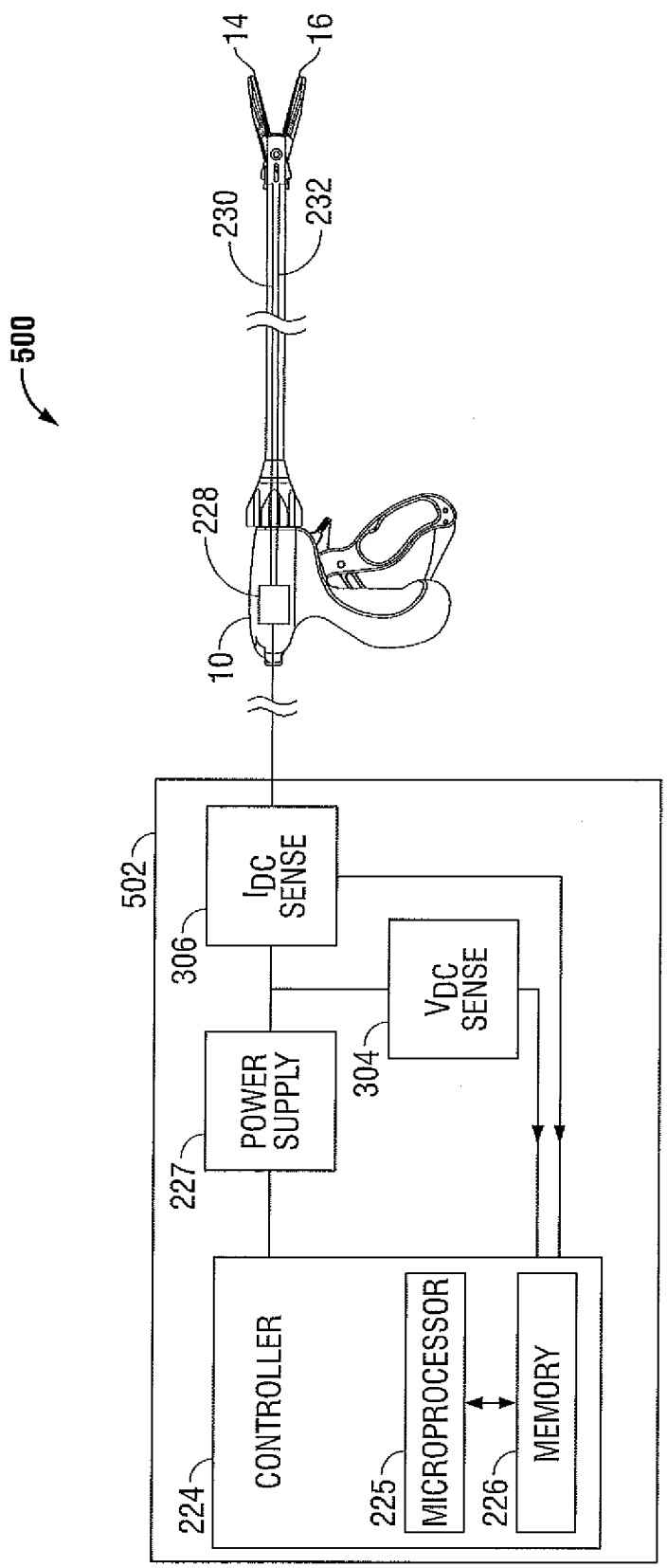
FIG. 5 is a schematic block diagram of an embodiment of an electrosurgical system according to the present disclosure.

FIG. 5 illustrates another embodiment of an electrosurgical system 500. The system 500 includes a generator 502, which is similar to the generator 200 described above with respect to FIGS. 2 and 3. The generator 502 is coupled to the forceps 10, which is shown for illustrative purposes only, and any other electrosurgical instrument may be utilized. The system 500 decouples the output stage 228 from the generator 502. The output stage 228 is instead disposed in the housing 11 of the forceps 10. The generator 502 also does not include RF voltage and current sensors 300 and 302, which allows for significant miniaturization of the output stage 228 and repositioning thereof into the housing 11. This significantly simplifies the hardware design for the electrosurgical system 500.

Calculation of output RF values based on measured DC signals also simplifies hardware and software requirements of electrosurgical generators, which usually perform intensive root mean square calculations. Further, this configuration obviates the need to include sensors at the high voltage side of the generator, allowing for use of components with a lower voltage rating.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   a direct current power supply configured to supply direct current;
   a radio frequency output stage electrically coupled to the direct current power supply, the radio frequency output stage includes at least one active output terminal and at least one return output terminal and is configured to transform direct current into a radio frequency waveform;
   a direct current voltage sensor coupled to the direct current power supply and configured to measure direct current voltage;
   a direct current current sensor coupled to the direct current power supply and configured to measure direct current;
   a controller coupled to the direct current voltage and current sensors, the controller configured to determine at least one of voltage and current of the radio frequency waveform based on the measured voltage and current of the direct current;
   a radio frequency voltage sensor coupled to the at least one active output terminal and the at least one return output terminal and configured to measure radio frequency voltage therebetween; and
   a radio frequency current sensor coupled to the at least one active output terminal and configured to measure radio frequency current therethrough,
   wherein the controller is configured to compare at least one of calculated voltage and calculated current of the radio frequency waveform with at least one of measured voltage and measured current of the radio frequency waveform.

2. The electrosurgical system according to claim 1, wherein the controller is configured to determine a dosage error based on the comparison.

3. The electrosurgical system according to claim 1, wherein the radio frequency output stage is disposed within a housing of a handheld electrosurgical instrument.

4. The electrosurgical system according to claim 3, wherein the handheld electrosurgical instrument is an electrosurgical forceps including at least one shaft member having an end effector assembly disposed at a distal end thereof, the end effector assembly including two jaw members movable from a first position in spaced relation relative to one another to at least one subsequent position wherein the jaw members cooperate to grasp tissue therebetween, each of the jaw members including an electrically conductive sealing surface.

5. The electrosurgical system according to claim 1, wherein the controller determines at least one of the voltage and the current of the radio frequency waveform based on the direct current voltage and direct current using a transfer function that correlates the direct current voltage and direct current to at least one of the voltage and the current of the radio frequency waveform.

6. A method for delivering radio frequency energy to tissue, the method comprising:
   generating direct current at a direct current power supply;
   transforming direct current into a radio frequency waveform at a radio frequency output stage electrically coupled to the direct current power supply;
   measuring voltage and current of the direct current supplied to the radio frequency output stage;
   determining at least one of voltage and current of the radio frequency waveform based on the measured voltage and current of the direct current;
   measuring voltage and current of the radio frequency waveform; and
   comparing calculated voltage and current of the radio frequency waveform, based on the measured voltage and current of the direct current, with measured voltage and current of the radio frequency waveform.

7. The method according to claim 6, further comprising:
   calculating a dosage error based on the comparison, wherein the dosage error is a difference between the calculated voltage and current of the radio frequency waveform and the measured voltage and current of the radio frequency waveform, respectively.

8. The method according to claim 6, further comprising:
   performing at least one of issuing an alarm, adjusting or terminating output of at least one of the power supply and the radio frequency output stage based on the dosage error.

9. The method according to claim 6, wherein the determining includes calculating at least one of voltage and current of the radio frequency waveform based on the measured voltage and current of the direct current using a transfer function that correlates the direct current voltage and direct current to at least one of the voltage and the current of the radio frequency waveform.

10. An electrosurgical system, comprising:
an electrosurgical generator including:
- a direct current power supply configured to supply direct current;
- a direct current voltage sensor coupled to the direct current power supply and configured to measure direct current voltage;
- a direct current current sensor coupled to the direct current power supply and configured to measure direct current;
- a controller coupled to the direct current voltage and current sensors; and an electrosurgical instrument coupled to the electrosurgical generator, the electrosurgical instrument including:
- a radio frequency output stage electrically coupled to the direct current power supply, the radio frequency output stage includes at least one active output terminal and at least one return output terminal, the radio frequency output stage is configured to transform direct current into a radio frequency waveform, wherein the controller is configured to determine at least one of voltage and current of the radio frequency waveform based on the measured voltage and current of the direct current;
- a radio frequency voltage sensor coupled to the at least one active output terminal and the at least one return output terminal and configured to measure radio frequency voltage therebetween; and
- a radio frequency current sensor coupled to the at least one active output terminal and configured to measure radio frequency current therethrough,
  wherein the controller is configured compare at least one of calculated voltage and calculated current of the radio frequency waveform with at least one of measured voltage and measured current of the radio frequency waveform, respectively.

11. The electrosurgical system according to claim 10, wherein the electrosurgical instrument is an electrosurgical forceps including at least one shaft member having an end effector assembly disposed at a distal end thereof, the end effector assembly including two jaw members movable from a first position in spaced relation relative to one another to at least one subsequent position wherein the jaw members cooperate to grasp tissue therebetween, each of the jaw members including an electrically conductive sealing surface.

12. The electrosurgical system according to claim 11, wherein the controller is configured to determine a dosage error based on the comparison.

* * * * *